United States Patent [19]
Rabo et al.

[11] Patent Number: 4,652,538
[45] Date of Patent: Mar. 24, 1987

[54] CATALYSTS FOR CONVERSION OF SYNGAS TO LIQUID MOTOR FUELS

[75] Inventors: Jule A. Rabo, Armonk; Peter K. Coughlin, Yorktown Heights, both of N.Y.

[73] Assignee: Union Carbide Corporation, Danbury, Conn.

[21] Appl. No.: 780,259

[22] Filed: Sep. 26, 1985

Related U.S. Application Data

[63] Continuation-in-part of Ser. No. 547,668, Nov. 1, 1983, abandoned.

[51] Int. Cl.$^4$ .......................... B01J 29/10; B01J 29/20
[52] U.S. Cl. .......................................... 502/66; 502/74
[58] Field of Search ........................ 502/64, 74, 79, 66

[56] References Cited

U.S. PATENT DOCUMENTS

| 3,013,990 | 12/1961 | Breck et al. | 502/74 |
|---|---|---|---|
| 4,157,338 | 6/1979 | Haag et al. | 502/74 |
| 4,192,777 | 3/1980 | Vicker | 252/457 |
| 4,207,248 | 6/1980 | Butter et al. | 518/719 |
| 4,279,830 | 7/1981 | Haag et al. | 518/700 |
| 4,292,415 | 9/1981 | Vollhardt | 525/357 |
| 4,443,552 | 4/1984 | Iida et al. | 502/66 |
| 4,556,645 | 12/1985 | Coughlin et al. | 502/66 |

FOREIGN PATENT DOCUMENTS 874373 2/1979 Belgium .

OTHER PUBLICATIONS

"The Fischer-Tropsch Synthesis" Catalysis, Chapter 4, pp. 159-255, see Table 9 on p. 183.
"Synthesis Gas Conversion to Aromatic Hydrocarbons" Journal of Catalysis, 56,268-273 (1979) ZSM-5.
"Catalysts Obtained by Reaction of Transition-Element-Organometallic Compounds with Oxide-Support Surfaces, Catalytic Properties of Systems . . . " A. S. Lisitsyn et al. (1983).
"Effect of the Type of Carrier on the Properties of Cobalt Catalysts in the Synthesis of Aliphatic Hydrocarbons from Carbon Monoxide and Hydrogen" (1981).
"Selective Formation of Propene from CO+$H_2$ or $C_2H_4$ with $Fe_3(CO)_{12}$ Supported on Inorganic Oxides" J.C.S. Chem. Comm. pp. 719-721 (1980).
"New Evidence for the Mechanism of the Fischer-Tropsch Synthesis of Hydrocarbons" Journal of Catalysis 66, 401-411 (1980).
Alumina-Supported CO Hydrogenation Catalysts Prepared from Molecular Osmium and Ruthenium Clusters, Faraday Discussion 72 (1981).
"Iron Alloy Fischer-Tropsch Catalysts" Journal of Catalysis 72, 95-110 (1981).

Primary Examiner—Carl F. Dees
Attorney, Agent, or Firm—Gary L. Wamer

[57] ABSTRACT

Synthesis gas comprising carbon monoxide and hydrogen is converted to $C_5{}^+$ hydrocarbons suitable for use as liquid motor fuels by contact with a dual catalyst composition capable of ensuring the production of only relatively minor amounts of heavy products boiling beyond the diesel oil range. The catalyst composition, having desirable stability during continuous production operation, employs a Fischer-Tropsch catalyst, together with a co-catalyst/support component. The latter component is a steam-stabilized zeolite Y catalyst of hydrophobic character, desirably in acid-extracted form.

33 Claims, No Drawings 4,652,538

CATALYSTS FOR CONVERSION OF SYNGAS TO LIQUID MOTOR FUELS

STATEMENT

The Government of the United States of America has rights to this invention pursuant to Contract No. DE-AC22-81PC40077 awarded by the U.S. Department of Energy.

REFERENCE TO RELATED APPLICATION

This application is a continuation-in-part of applicants' earlier application Ser. No. 547,668 filed Nov. 1, 1983, now abandoned, entitled "CONVERSION OF SYNGAS TO LIQUID MOTOR FUELS".

BACKGROUND OF THE INVENTION

1. Field of the Invention

The invention relates to the conversion of synthesis gas to hydrocarbons. More particularly, it relates to the conversion of such synthesis gas to $C_5^+$ hydrocarbons particularly suitable for use as liquid motor fuels.

2. Description of the Prior Art

It is well known in the art that synthesis gas, i.e., hydrogen and carbon monoxide, can be converted to hydrocarbons in the presence of a variety of transition metal catalysts. Thus, certain Group VIII metals, particularly iron, cobalt, ruthenium and nickel, are known to catalyze the conversion of CO and hydrogen, also referred to as syngas, to hydrocarbons. Such metals are commonly called Fischer-Tropsch catalysts. While the use of nickel preferentially produces methane upon conversion of syngas; the use of iron, cobalt and ruthenium tends to produce hydrocarbon mixtures consisting of hydrocarbons having a larger carbon number than methane, as determined by a number of analytical means including mass spectrographic analysis of individual components and the boiling point curve method. At higher reaction temperatures, all Fischer-Tropsch catalysts tend to produce gaseous hydrocarbons, and it is readily feasible to select processing conditions to produce methane as the principal product. At lower temperatures, and usually at higher pressures, however, iron, cobalt and ruthenium produce hydrocarbon mixtures consisting of larger hydrocarbons. The products usually contain very long straight-chain hydrocarbon molecules that tend to precipitate as wax. Such wax material, boiling well beyond the boiling range of motor fuels, typically constitutes a significant fraction of the product produced in such catalytic conversion operations. Fischer-Tropsch catalysts, therefore, have not been advantageously employed in the production of liquid hydrocarbon motor fuels, since they have commonly produced either principally gaseous hydrocarbons, on the one hand, or hydrocarbons containing an unacceptably large amount of wax on the other. In addition, the gasoline boiling hydrocarbon fraction produced has an unacceptably low octane number.

In light of such circumstances, efforts have been made to improve the performance of Fischer-Tropsch catalysts for use in various desired syngas conversions. For example, the Breck et al. patent, U.S. Pat. No. 3,013,990, discloses the use of zeolitic molecular sieves containing a Fischer-Tropsch catalyst as improved catalyst compositions. Thus, Type A, X and Y molecular sieves loaded with iron or cobalt are shown to be suitable Fischer-Tropsch hydrocarbon synthesis catalysts. With respect to the conversion of syngas, Fraenkel et al., U.S. Pat. No. 4,294,725, teach that zeolites A and Y loaded with cobalt, incorporated by ion exchange and reduced in-situ with cadmium, serve as useful catalysts of the Fischer-Tropsch type. Those skilled in the art will appreciate that such catalyst materials tend to be relatively expensive and, in any event, do not produce hydrocarbon products advantageous for use as liquid motor fuels.

Efforts have also been made to improve Fischer-Tropsch catalyst performance by preparing intimate mixtures of Fischer-Tropsch metals, such as iron, with an acidic crystalline aluminosilicate, such as ZSM-5. The Chang et al. patents, U.S. Pat. No. 4,086,262, and U.S. Pat. No. 4,096,163, disclose such catalyst compositions employed in the conversion of synthesis gas to hydrocarbon mixtures useful in the manufacture of heating fuels, gasoline, aromatic hydrocarbons and chemical intermediates. When it is desired to convert syngas specifically to hydrocarbons boiling in the jet fuel+diesel oil boiling range, however, such an approach is not suitable, experiencing an effective limitation at $C_{10}$ carbon number as was the case using ZSM-5 in methanol conversion, as disclosed in the Owen et al. patent, U.S. Pat. No. 3,969,426.

Another difficulty present in the production of liquid motor fuels, particularly those boiling in the gasoline boiling range, by the conversion of syngas in the presence of Fischer-Tropsch metal catalysts is the tendency of such Fischer-Tropsch metals to characteristically produce straight chain hydrocarbons consisting of a mixture of n-paraffins and n-olefins. The actual mixture obtained will be understood to depend upon the particular metal catalyst and the process conditions employed. In any event, the conversion product will generally contain only small amounts of mono-branched and almost no multi-branched hydrocarbons, as well as very little naphthenes and aromatics. The absence of branched or aromatic, i.e. cyclic, hydrocarbons in the conversion products results in such products having gasoline fractions of very low octane number, or O.N. Such fractions are not suitable for use as gasoline without the addition of further, expensive refining steps. The larger n-paraffins produced in the $C_{10}$–$C_{18}$ range by such metal catalysts are, of course, desirable components for incorporation in jet and diesel fuels. However, the presence of some branched and aromatic hydrocarbons are also desired in such components to enhance the thermal efficiency of the overall process for converting raw syngas to such liquid motor fuels and to reduce the pour point of such fuels. In addition, the accompanying production of hydrocarbon products boiling above the diesel oil range, when the Fischer-Tropsch metal catalyst is not encumbered in its effect by the presence of a zeolite, such as ZSM-5, constitutes a recognized economic and marketing burden.

The use of iron-or-cobalt-loaded molecular sieves as Fischer-Tropsch catalysts is disclosed by Breck et al, U.S. Pat. No. 3,013,990. Numerous molecular sieves are disclosed for such purposes, including zeolite A, D, L, S, T, X, Y and others, but with no indication as to the nature of the products produced by such iron-or-cobalt-loaded molecular sieve catalyst compositions used as Fischer-Tropsch catalysts. Breck et al contain no indication as to whether such molecular sieve compositions in general, or those using zeolite Y in particular, would have a useful life such as to be of practical commercial significance. Nor is there any indication as to whether any form of such molecular sieve materilas might be more useful than another form thereof when employed in a Fischer-Tropsch catalyst.

The Brennan patent, U.S. Pat. No. 4,269,783 discloses the use of strong acid Y zeolite in Fischer-Tropsch catalysis, but without reference to the conversion of syngas to liquid motor fuels boiling in the gasoline and jet fuel+diesel oil boiling range. The usual form of Y zeolite that is used in catalysis is such a strong acid form of Y zeolite, such as calcined ammonium Y, which may be (1) ion exchanged with multivalent cations and/or steamed to enhance the stability thereof, or (2) calcined ammonium exchanged, steamed Y, marketed by Union Carbide Corporation under the designation LZ-Y82. Said LZ-Y82 is representative of the zeolite Y catalysts known as possessing outstanding catalytic properties in petroleum refining, as in catalytic cracking and hydrocracking processes. Despite such properties, LZ-Y82 has been found to have a low activity for methanol conversion in a fixed bed reactor configuration because of its rapid coking tendencies. The stability of a catalyst will be understood to constitute a significant factor in the evaluation of that catalyst for a given purpose. Thus, the rapid coking of said LZ-Y82 material renders it unstable and unsuitable for said methanol conversion purposes. Because of its known catalytic properties in petroleum refining applications, LZ-Y82 was also employed in the on-going effort described above to develop a process and related catalyst composition suitable for the conversion of syngas to liquid motor fuels boiling in the gasoline and jet fuel+diesel oil boiling range. Fischer-Tropsch metal/LZ-Y82 co-catalyst/support compositions have been found to convert syngas to a desirable hydrocarbon product containing $C_{10}^+$ hydrocarbon molecules up to about $C_{22}$ material. Those skilled in the art will appreciate that gasoline boiling range material extends up to $C_{10}$ and that jet fuel+diesel oil range material comprises $C_{10}^+$ hydrocarbons up to about $C_{22}$ material. The Fischer-Tropsch metal (cobalt)/LZ-Y82 catalyst composition, when employed for such syngas conversion purposes, was found to experience an initial period of rapid deactivation, as is quite common in the performance of hydrocracking catalysts and other commercial catalysts. Such catalysts then commonly experience a much longer period of slow deactivation that is of significance in evaluating the commercial usefulness of the catalyst. In the use of acid cobalt/LZ-Y82 catalyst composition, such slow deactivation, following the expected rapid initial deactivation, was found to be sustained, with the deactivation rate appearing to increase over the course of continuous processing operations, such as to render the catalyst composition generally unsuitable for the subject syngas conversion operations because of this continued loss of catalytic activity, i.e. stability, over a period of time which is unacceptable from a commercial viewpoint.

For the reasons above, the development of improved technology for the conversion of syngas to liquid hydrocarbon fuels is desired in the art. Such improved technology would desirably enable such syngas conversion to be carried out with (1) enhanced branching and aromatization as compared with the present production of predominately n-paraffins and n-olefins, and (2) enhanced production of desired liquid motor fuels by reducing the formation of methane and of heavy hydrocarbon products boiling beyond the boiling range of diesel oil. At the same time, the catalyst composition must have a requisite degree of activity and stability to enable the production of such motor fuels to be carried out in practical commercial operations.

It is an object of the invention, therefore, to provide an improved process and catalyst composition for the conversion of syngas to liquid hydrocarbon motor fuels.

It is another object of the invention to provide a stable catalyst composition capable of enhancing the conversion of syngas to such liquid fuels.

It is a further object of the invention to provide a process and Fischer-Tropsch catalyst composition for producing liquid motor fuels containing minimal amounts of methane and of heavy hydrocarbon products boiling beyond the boiling range of diesel oil.

With these and other objects in mind, the invention is hereinafter described in detail, the novel features thereof being particularly pointed out in the appended claims.

SUMMARY OF THE INVENTION

Synthesis gas is converted to liquid motor fuels in the practice of the invention by the use of a dual catalyst composition containing a Fischer-Tropsch metal as a component thereof. A particular steam-stabilized zeolite Y catalyst is employed as a co-catalyst/support component. The conversion product contains minimal amounts of methane and of heavy products boiling beyond the boiling range of diesel oil.

DETAILED DESCRIPTION OF THE INVENTION

The objects of the invention are accomplished by employing a Fischer-Tropsch metal in combination with a particular hydrophobic zeolite Y catalyst in the conversion of syngas to liquid hydrocarbons. Contrary to the results previously obtained by the use of Fischer-Tropsch catalysts for syngas conversion, the use of such a novel catalyst composition results in an advantageous production of liquid motor fuels boiling in the jet fuel plus diesel oil boiling range. As the castalyst composition is found to have outstanding stability over the course of continuous processing operations, the catalyst composition and the process for its use for syngas conversion, as herein described and claimed, represent a highly desirable and practical approach to the desired production of liquid motor fuels boiling in the gasoline, jet fuel+diesel oil boiling range.

The synthesis gas, or syngas, treated in accordance with the practice of the invention generally comprises a mixture of hydrogen and carbon monoxide, although smaller amounts of carbon dioxide, methane, nitrogen and other components may also be present as will be well known to those skilled in the art. Syngas is commonly produced by the partial oxidation of coal and pertroleum deposits, or by similar gasification of other carbonaceous fuels such as peat, wood and cellulosic waste materials. The hydrogen/carbon oxide volume ratio of such syngas is desirably in the range of from about 0.2/1 to about 6.0/1 prior to conversion as herein disclosed and claimed. This ratio can be adjusted, if desired, by reaction of carbon monoxide with steam in the well-known water-gas shift reaction. If required, sulfur impurities can be removed from the syngas mixture by conventional means known in the art. It should also be noted that the syngas as described herein includes art-recognized equivalents, such as mixtures of carbon monoxide and steam, or of carbon dioxide and hydrogen, that can provide synthesis gas mixture by in-situ reaction under the operating conditions employed.

The dual catalyst composition of the invention, employed as described herein for the conversion of syngas to liquid motor fuels, contains a Fischer-Tropsch metal as a component thereof. Various Group VIII metals known to catalyze the conversion of syngas to hydrocarbons, and commonly referred to as Fischer-Tropsch catalysts, may be employed in the practice of the invention, e.g. iron, cobalt, ruthenium and nickel as well as molybdenum, tungsten, rhenium and the like. It has been found that, on an overall evaluation basis, the use of iron and of cobalt as the Fischer-Tropsch metal component of the catalytic composition is particularly desirable for purposes of the invention.

The second principal component of the catalyst composition of the invention is a steam-stabilized zeolite Y catalyst of hydrophobic character, employed as a cocatalyst and optionally as a support for the metal component of the composition. Some such zeolite Y compositions have been referred to in the art as ultrahydrophobic type Y zeolites, or simply as UHP-Y zeolites. The Y zeolites used in this invention are prepared by extensive steaming of the low-sodium forms of zeolite Y substantially as described in Belgian Pat. No. 874,373, issued Feb. 22, 1979. Such zeolites are organophilic zeolitic aluminosilicate compositions having a $SiO_2$—$Al_2O_3$ molar ratio equal to or greater than 4.5, an an essential X-ray powder diffraction pattern of zeolite Y. Furthermore, the zeolites have a crystallographic unit cell dimension, $a_o$, of less than 24.45 Angstroms, a sorptive capacity for water vapor at 25° C. and a $p/p_o$ value of 0.10 of less than 10.0 weight percent. In preferred compositions, said unit cell dimension of the catalyst is from 24.20 to 24.35 Angstroms. In addition, the water adsorption capacity at 25° C. and a $p/p_o$ value of 0.10 is desirably less than 4.0 weight percent. More particularly, the $SiO_2$—$Al_2O_3$ molar ratio for certain embodiments is from 4.5 to 20.0. In a desirable embodiment in which the UHP-Y zeolite is acid extracted as discussed below, the $SiO_2$—$Al_2O_3$ molar ratio may be extended up to about 100 or more, as the alumina content of the zeolite is generally reduced to less than about 3 weight % or even to about 1 weight % or less in practical commercial applications.

For the determination of the sorptive capacity of the hydrophobic zeolite Y compositions for any particular adsorbate, e.g. water, the test zeolite sample is activated by preheating at 425° C. for 16 hours at a pressure of 5 micrometers of mercury in a conventional McBain apparatus. The temperature of the sample is thereafter adjusted to the desired value and contacted with the vapor of the test adsorbate at the desired pressure.

The hydrophobic zeolites suitable for purposes of the invention, as described above, have also been found especially suited for use as adsorbents in applications where it is desired to preferentially adsorb organic constituents from solutions or mixtures thereof with water. In the formation of synthesis gas by the distillation of coal for example, it is desirable, for environmental and economic reasons, to recover the relatively small portion of phenol present in the condensate fraction of principally water that is produced therein. For this purpose, the condensate can be contacted at ambient temperature with said hydrophobic zeolite that will selectively adsorb the phenol from said condensate. Such zeolites have also been found highly suitable for use as base materials for catalyst compositions having important commercial applications, e.g. in midbarrel hydrocracking catalyst compositions. The UHP-Y zeolites, described in particular detail in the Belgian patent referred to above and incorporated herein by reference, are not very active catalytically and have found only limited catalytic applications, although they have been found active for the conversion of methanol to hydrocarbons ranging from methane to those boiling in the jet fuel and diesel oil boiling range up to about $C_{22}$ material.

The invention is hereinafter described with reference to certain specific examples that are presented to illustrate various embodiments, but that should not be construed as limiting the scope of the invention as set forth in the appended claims.

EXAMPLE I

The advantageous conversion of syngas obtainable by the practice of the invention is illustrated by the following comparative examples based on the conversion of syngas to $C_5^+$ hydrocarbons. In each case, the reaction was carried out in an internal recirculation reactor, with about 80 cc. of catalyst used in each run. The synthesis gas fed to the reactor in each case was composed of a mixture of carbon monoxide, hydrogen and argon. Argon was used as an inert tracer to facilitate computations of material balance and conversion. The synthesis gas had a composition of about 60% hydrogen, 30% CO, 10% argon, all in mole percent. The synthesis gas was fed to the reactor during each run at a rate of about 400 GHSV, i.e. gas hourly space velocity, or volume of gas (at 0° C., 1 atm)/volume catalyst/hour. The conversion reaction was carried out a pressure of about 300 psig. and at a temperature range of 240°-310° C. Product samples of effluent gas and liquids were generally collected once a day. The liquid product generally had two layers, i.e. an aqueous layer and an organic oily layer, sometimes having contained solids or crystals associated therewith. The effluent gases were analyzed by gas chromatography for light hydrocarbons and fixed gases, e.g. hydrogen, CO, argon, $CO_2$ and the like. The products in the oil layers were characterized by FIA, i.e. Florescence Indicator Absorption for weight olefins, saturates and oxygenates, and by simulated distillation for boiling point distribution.

Prior to syngas conversion, Fischer-Tropsch synthesis catalysts are commonly reduced or activated with hydrogen or a hydrogen-containing gas at a temperature of approximately 450° C. or lower and a pressure of from 0 psig. to the synthesis gas operating pressure, after which the catalyst material is subjected to carbiding with a low $H_2$/CO ratio gas at a temperature of approximately 250° C. and at pressures up to synthesis operating pressure. This activation approach was not employed, however, in preparing any of the samples for the comparative runs described below with respect to Example I.

It is also possible to activate the catalyst by carbiding first with low $H_2$/CO ratio gas, or with CO alone, at a temperature in the range of 250°-320° C. and a pressure of from 0 psig to synthesis operating pressure, followed by hydrogen treatment at similar temperature and pressure. This procedure was employed in preparing the catalyst samples for the comparative runs described below.

Three different catalyst compositions were employed in comparative runs, each comprising the same Fischer-Tropsch metal as a carbon monoxide reducing component, i.e., iron precipitated on the co-catalyst/support, but employing a different co-catalyst/support component. Thus, catalyst composition A employed α-alumina, with the Fe-α-alumina composition containing 39% Fe by weight, said Fe being precipitated on said α-alumina. Catalyst composition B employed amorphous silica-alumina ($SiO_2$—$Al_2O_3$) as the co-catalyst/support with the resulting Fe-amorphous silica-alumina composition containing 45% Fe by weight. The Fe was similarly precipitated on the silica-alumina support. Catalyst composition C utilized a steam-stabilized, ultrahydrophobic zeolite Y, i.e., UHP-Y zeolite, as the co-catalyst/support component, with the resulting Fe-UHP-Y zeolite composition containing 30% by weight Fe, said Fe again being precipitated on the Zeolite Y support. The experimental catalysts so provided were designed to evaluate the characteristics of such UHP-Y zeolite as a co-catalyst in the conversion of syngas to liquid fuels. Since acid catalysts such as zeolites have no catalytic activity, by themselves, to reduce CO by means of hydrogen, the UHP-Y material must necessarily be combined in the finished catalyst mix with a Fischer-Tropsch metal catalyst, e.g., iron, well known for its catalytic activity in the syngas conversion reaction. In order to assess the specific catalyst characteristics of said UHP-Y in the catalyst compositions for comparison, the reference catalysts were prepared with the following objective:

Fe-α-alumina catalyst- This catalyst was intended to provide a presumably catalytically inert matrix (α-alumina) similar in crystal size to UHP-Y. The use of a similar amount and similar crystal size of the matrix material would provide a similar dispersion of the iron catalyst in both the α-alumina and the UHP-Y catalysts. This enables a distinction to be made between the intrinsic catalytic effect of UHP-Y and its effect on the dispersion of the iron catalyst, since it is known in the art that the extent of the iron dispersion influences catalytic activity.

Fe-silica-alumina gel catalyst- In the preparation of this catalyst, the iron was applied in a similar concentration to that applied with respect to the UHP-Y and the α-alumina type support materials. This was done to keep the iron in a similar state in all three catalyst compositions. The silica-alumina additive was employed to compare this well known acid catalyst with the use of said UHP-Y as a co-catalyst/support component.

The results of such comparative runs in terms of the conversion of syngas, i.e., (CO+$H_2$), the primary product selectivity between hydrocarbons and $CO_2$, the hydrocarbon selectivity of the desirable $C_5$+ range and other supplemental product characterizations are shown in Tables I, II and III below with respect to runs employing compositions, A, B and C, respectively, under the various operating conditions recited in each Table.

TABLE I

| Composition A (α-alumina) | | | | |
|---|---|---|---|---|
| Run | 1 | 2 | 3 | 4 |
| Hours on Stream | 24.20 | 47.94 | 71.31 | 94.96 |
| Temperature, °C. | 284 | 308 | 248 | 282 |
| Feed, cc/min. | 672 | 663 | 631 | 600 |
| Conversion wt. % | | | | |
| on CO | 83.91 | 88.28 | 16.87 | 62.84 |
| on $H_2$ | 49.45 | 50.55 | 16.88 | 40.48 |
| on (CO + $H_2$) | 61.12 | 63.18 | 16.88 | 48.02 |
| Product Selectivity, Wt. % | | | | |
| $CH_4$ | 28.92 | 37.24 | 27.79 | 29.67 |
| $C_2$-$C_4$ | 51.52 | 48.98 | 50.68 | 52.47 |
| Total $C_1$-$C_4$ | 80.44 | 86.22 | 78.47 | 82.14 |
| $C_5$-420° F. | 18.73 | 13.40 | 20.58 | 17.04 |
| 420° F.-700° F. | 0.80 | 0.36 | 0.90 | 0.78 |
| 700° F.-end point | 0.03 | 0.02 | 0.04 | 0.04 |
| $C_5$-end point | 19.56 | 13.78 | 21.53 | 17.86 |
| Iso/normal mole ratio: | | | | |
| $C_4$ | 0.1022 | 0.1188 | 0.0546 | 0.863 |
| $C_5$ | 0.2013 | 0.2348 | 0.1364 | 0.1730 |
| $C_6$ | 0.4084 | 0.3949 | 0.9910 | 0.9883 |
| FIA: | | | | |
| Aromatic | 10.1 | — | — | 6.1 |
| Olefin | 1.3 | — | — | 5.3 |
| Saturates | 88.6 | — | — | 88.6 |

TABLE II

| Composition B (Amorphous silica-alumina) | | | | | | |
|---|---|---|---|---|---|---|
| Run | 1 | 2 | 3 | 4 | 5 | 6 |
| Hours on Stream | 24.57 | 48.26 | 95.83 | 168.17 | 192.11 | 215.99 |
| Temperature, °C. | 282 | 282 | 309 | 251 | 281 | 281 |
| Feed, cc/min. | 782 | 782 | 782 | 782 | 782 | 782 |
| Conversion wt. % | | | | | | |
| on CO | 69.98 | 65.20 | 84.13 | 23.97 | 59.25 | 62.73 |
| on $H_2$ | 40.33 | 38.88 | 46.76 | 18.53 | 36.86 | 36.59 |
| on (CO + $H_2$) | 50.16 | 47.65 | 58.92 | 20.26 | 44.33 | 44.99 |
| Product Selectivity, Wt. % | | | | | | |
| $CH_4$ | 39.03 | 38.47 | 57.35 | 26.78 | 38.65 | 39.09 |
| $C_2$-$C_4$ | 51.30 | 52.28 | 37.36 | 54.18 | 51.43 | 50.17 |
| Total $C_1$-$C_4$ | 90.33 | 90.75 | 94.71 | 80.96 | 90.08 | 89.26 |
| $C_5$-420° F. | 9.67 | 9.25 | 5.29 | 19.03 | 9.90 | 10.73 |
| 420° F.-700° F. | 0.00 | 0.00 | 0.00 | 0.01 | 0.01 | 0.01 |
| 700° F.-end point | 0.00 | 0.00 | 0.00 | 0.00 | 0.00 | 0.00 |
| $C_5$-end point | 9.67 | 9.25 | 5.29 | 19.04 | 9.92 | 10.74 |
| Iso/normal mole ratio: | | | | | | |
| $C_4$ | 0.0639 | 0.0594 | 0.1057 | 0.0266 | 0.0646 | 0.0583 |
| $C_5$ | 0.1852 | 0.1687 | 0.3821 | 0.0765 | 0.1477 | 0.2170 |
| $C_6$ | 0.7532 | 0.5714 | 0.6753 | 0.7503 | 0.7237 | 0.4886 |

TABLE III

| Composition C (UHP-Y) | | | | | |
|---|---|---|---|---|---|
| Run | 1 | 2 | 3 | 4 | 5 |
| Hours on Stream | 46.08 | 70.90 | 94.09 | 140.15 | 169.02 |
| Temperature, °C. | 285 | 285 | 310 | 246 | 279 |
| Feed, cc/min. | 566 | 565 | 564 | 564 | 582 |

TABLE III-continued

| | Composition C (UHP-Y) | | | | |
|---|---|---|---|---|---|
| Run | 1 | 2 | 3 | 4 | 5 |
| Conversion wt. % | | | | | |
| on CO | 37.73 | 35.17 | 49.94 | 18.37 | 37.03 |
| on $H_2$ | 28.85 | 29.04 | 31.45 | 18.24 | 30.89 |
| on (CO + $H_2$) | 31.66 | 31.04 | 37.50 | 18.28 | 32.97 |
| Product Selectivity, Wt. % | | | | | |
| $CH_4$ | 27.53 | 26.88 | 56.30 | 19.16 | 22.99 |
| $C_2-C_4$ | 49.87 | 49.76 | 20.49 | 34.47 | 46.41 |
| Total $C_1-C_4$ | 77.40 | 76.64 | 76.79 | 58.63 | 69.40 |
| $C_5$–420° F. | 22.56 | 22.64 | 23.14 | 36.43 | 28.77 |
| 420° F.–700° F. | 0.04 | 0.65 | 0.07 | 4.67 | 1.63 |
| 700° F.–end point | 0.00 | 0.06 | 0.01 | 0.27 | 0.20 |
| $C_5$–end point | 22.60 | 23.36 | 23.21 | 41.37 | 30.60 |
| Iso/normal mole ratio: | | | | | |
| $C_4$ | 0.0893 | 0.0735 | 0.1313 | 0.0526 | 0.0650 |
| $C_5$ | 0.3084 | 0.2728 | 0.6515 | 0.0752 | 0.1344 |
| $C_6$ | 1.2393 | 1.2713 | 2.2649 | 1.1590 | 1.0045 |
| FIA: | | | | | |
| Aromatic | — | 34.8 | — | 9.7 | 16.7 |
| Olefin | — | 4.5 | — | 21.4 | — |
| Saturates | — | 60.6 | — | 68.8 | 83.3 |

Those skilled in the art will appreciate that the gasoline end point is about 420° F., while the diesel oil end point is about 700° F. It will also be appreciated that 420°–700° F. hydrocarbon material comprises molecules with more carbon atoms than $C_{10}$ hydrocarbons up to about $C_{22}$ material. Hydrocarbon material in the $C_{22}-C_{28}$ range generally comprises heavy distillate material, with material above $C_{28}$ generally comprising wax.

It will be noted that the conversion levels achieved by composition C, at reaction temperatures of about 280° C. and 310° C. were not as high as those achieved using Compositions A and B. Since the acid catalyst component does not catalyze the reduction of the CO by the $H_2$ present in the syngas mixture, the lower activity of the UHP-Y-based catalyst composition C for the conversion of CO is believed due to the somewhat lower iron content (30%) in said Composition C as compared to the higher iron content levels, namely 39% and 45%, of Compositions B and C, respectively. Very significantly, however, Composition C achieved superior results to the other two catalyst compositions at all of the temperature levels with respect both to (1) the CO selectivity to desired hydrocarbons and (2) the hydrocarbon selectivity to $C_5+$ liquid yields. Composition C will also be seen to have provided a product slate favoring the isomers, for butanes, pentanes and hexanes, when the reaction temperature reached the suitable level for the conversion of normal hydrocarbons to branched isomers, i.e., at temperatures of generally about 250° C. and above.

A hydrocarbon product slate containing significant amounts of aromatics in the condensed liquid product samples, which nevertheless represented only a small fraction of the total hydrocarbon product, was achieved using Composition C as is shown by FIA results from runs 2 and 5 as set forth in Table III (average 25.8 wt. % aromatics) when compared with the results obtained in runs 1 and 4 using Composition A, i.e., average 8.1 wt. % aromatics at substantially the same average reaction temperature level of about 283° C. By comparison, the quantity of $C_5+$ liquid hydrocarbons produced using Composition B was insufficient to enable FIA characterization to be made thereon.

Since catalyst deactivation is always a matter of concern in practical commercial operations, the stability of Composition C was determined by observing the conversions and selectivities obtained at 280° C. over the course of the run. Said Composition C was found to be quite stable throughout the duration of the tests, that over the course of 167 hours. The selectivities for hydrocarbons and $C_5+$ liquid yields actually showed a slightly tendency to improve with time on stream for Composition C, a feature not occurring in the runs using Compositions A or B.

EXAMPLE II

Additional syngas conversion runs were carried out using cobalt as the Fischer-Tropsch metal in combination with UHP-Y as the co-catalyst/support material. The catalyst was prepared by precipitating $CoOxH_2O$ onto UHP-Y zeolite powder by the addition of sodium carbonate solution to a stirred 10% slurry of said UHP-Y powder in an aqueous cobalt nitrate solution. The cobalt-loaded zeolite powder was filtered and washed with hot distilled water, dried at 110° C. and calcined in air for two hours at 250° C. The resulting catalyst contained approximately 15% by weight cobalt. Prior to being used in the treatment of a syngas, the catalyst was activated by reduction at 350° C. and 300 psig for 24 hours using 1,000 cc/min of hydrogen. In one series of runs, a feed gas mixture of 50 mol % hydrogen and 50 mol % CO was employed, with the temperature being maintained essentially at about 219° C. and a pressure of 300 psig, with 400 cc/min of feed gas being employed in each run. The cobalt-containing catalyst employed throughout the series of runs had an initial weight of 31.4 grams. The results obtained are as set forth in Table IV below.

TABLE IV

| Run | 1 | 2 | 3 | 4 | 5 | 6 | 7 |
|---|---|---|---|---|---|---|---|
| Hours on Stream | 16.83 | 23.99 | 40.49 | 45.49 | 64.74 | 69.66 | 8.16 |
| Conversion wt. % | | | | | | | |
| on CO | 5.50 | 9.79 | 9.86 | 9.09 | 8.68 | 16.39 | 16.33 |

TABLE IV-continued

| Run | 1 | 2 | 3 | 4 | 5 | 6 | 7 |
|---|---|---|---|---|---|---|---|
| on $H_2$ | 18.76 | 27.53 | 28.15 | 27.20 | 25.69 | 30.35 | 30.26 |
| on (CO + $H_2$) | 12.18 | 18.75 | 18.97 | 18.10 | 17.28 | 23.34 | 23.26 |
| Product Selectivity, Wt. % | | | | | | | |
| $CH_4$ | 19.16 | 12.80 | 13.02 | 13.31 | 15.66 | 7.27 | 7.27 |
| $C_2$-$C_4$ | 15.63 | 12.60 | 11.43 | 10.50 | .06 | 4.92 | 5.01 |
| $C_5$-420° F. | 55.45 | 50.36 | 51.64 | 50.10 | 43.87 | 40.61 | 27.51 |
| 420° F.-700° F. | 9.14 | 22.73 | 22.33 | 22.07 | 26.21 | 39.93 | 34.73 |
| 700° F.-end point | 0.63 | 1.52 | 1.58 | 4.01 | 4.19 | 7.26 | 25.47 |
| $C_5$-end point | 65.21 | 74.60 | 75.55 | 76.19 | 74.28 | 87.81 | 87.72 |
| Iso/normal mole ratio: | | | | | | | |
| $C_4$ | 0.0000 | 0.0449 | 0.0529 | 0.0000 | 0.0000 | 0.0000 | 0.0000 |
| $C_5$ | 0.0000 | 0.0000 | 0.0426 | 0.0000 | 0.0000 | 0.0000 | 0.0000 |
| $C_6$ | 0.0598 | 0.1780 | 0.1047 | 0.0000 | 0.0000 | 0.0854 | 0.0000 |

In another set of runs, the results of which are set forth in Table V below, catalyst samples utilized as in the runs shown in Table IV were further used with additional quantities of the same feed gas mixture at a higher temperature of about 251°-253° C.

TABLE V

| Run | 1 | 2 | 3 | 4 | 5 | 6 | 7 |
|---|---|---|---|---|---|---|---|
| Hours on Stream | 95.49 | 112.49 | 119.74 | 136.32 | 143.90 | 160.40 | 167.57 |
| Conversion wt. % | | | | | | | |
| on CO | 46.28 | 43.09 | 38.45 | 37.80 | 39.93 | 39.13 | 39.35 |
| on $H_2$ | 68.52 | 66.38 | 64.11 | 63.94 | 65.41 | 64.73 | 63.11 |
| on (CO + $H_2$) | 57.17 | 54.54 | 51.28 | 50.83 | 52.61 | 51.87 | 50.87 |
| Product Selectivity, Wt. % | | | | | | | |
| $CH_4$ | 18.41 | 15.35 | 16.80 | 16.43 | 14.20 | 13.82 | 12.72 |
| $C_2$-$C_4$ | 11.66 | 10.22 | 11.61 | 11.22 | 10.38 | 10.06 | 9.29 |
| $C_5$-420° F. | 37.50 | 40.34 | 39.85 | 42.40 | 40.46 | 42.69 | 39.98 |
| 420° F.-700° F. | 27.44 | 25.06 | 26.85 | 23.83 | 29.58 | 26.18 | 32.16 |
| 700° F.-end point | 4.99 | 9.03 | 4.88 | 6.12 | 5.38 | 7.25 | 5.85 |
| $C_5$-end point | 69.93 | 74.43 | 71.59 | 72.35 | 75.42 | 76.12 | 77.99 |
| Iso/normal mole ratio: | | | | | | | |
| $C_4$ | 0.0432 | 0.0406 | 0.0401 | 0.0319 | 0.0358 | 0.0374 | 0.0364 |
| $C_5$ | 0.0784 | 0.0675 | 0.0657 | 0.0634 | 0.0794 | 0.0829 | 0.0797 |
| $C_6$ | 0.2313 | 0.2247 | 0.2234 | 0.2234 | 0.2338 | 0.2108 | 0.1993 |

Additional runs were carried out under similar conditions, but at a temperature of 284° C. employing samples previously used over the period of time indicated in Tables IV and V above, with the results of such further extended runs being set forth in Table VI below.

TABLE VI

| Run | 1 | 2 |
|---|---|---|
| Hours on Stream | 184.49 | 191.07 |
| Conversion wt. % | | |
| on CO | 76.96 | 73.19 |
| on $H_2$ | 90.81 | 89.79 |
| on (CO + $H_2$) | 83.78 | 81.44 |
| Product Selectivity, Wt. % | | |
| $CH_4$ | 32.05 | 34.98 |
| $C_2$-$C_4$ | 16.84 | 18.09 |
| $C_5$-420° F. | 31.29 | 33.30 |
| 420° F.-700° F. | 13.03 | 9.41 |
| 700° F.-end point | 6.79 | 4.22 |
| $C_5$-end point | 51.11 | 46.93 |
| Iso/normal mole ratio: | | |
| $C_4$ | 0.1202 | 0.1233 |
| $C_5$ | 0.3455 | 0.3264 |
| $C_6$ | 0.8357 | 0.8412 |

By comparison with the conversion, product selectivity and iso/normal ratio for the embodiment of the invention utilizing iron as the Fischer-Tropsch metal component, it will be seen that the cobalt-containing catalyst employed in Example II provides generally preferable syngas to liquid motor fuel performance, particularly at temperatures of approximately 250° C. as compared with the results at approximately 220° C. The results obtained in the practice of the invention were advantageous in any event, particularly upon consideration of the relatively low cobalt metal loading of about 15%, based on the overall weight of the catalyst employed. The high $H_2$/CO usage, as evidenced by the conversion on $H_2$ vis-a-vis the conversion on CO, indicates that the catalyst is not particularly efficient when employed in a 1/1 H/CO syngas mixture, because of a lack of water gas shift activity. Other tests employing a 2/1 syngas, however, demonstrated very efficient performance in this regard. It is also significant to note that the catalyst showed no sign of deactivation over the use of the extended run time of Example II.

On a carbon number basis, selectivity for the desired hydrocarbon product will be seen to be highly favorable, although an appreciable amount of methane is also produced. The $C_5^+$ yield will be seen to be excellent, accounting for over one half of the total hydrocarbon product obtained. Significantly, a very large portion of the hydrocarbons produced boil in the desired motor fuel range of $C_5$-700° F. The product quality of the motor fuels boiling in the $C_{10}$(350° F.)–$C_{18}$(700° F.), particularly in the $C_{12}$(420° F.)–$C_{18}$(700° F.), range suitable for jet and diesel fuels, produced during the Example II runs is good, illustrating the beneficial results obtainable in the practice of the invention.

EXAMPLE III

In this example using cobalt as the Fischer-Tropsch metal catalyst, the steam-stabilized zeolite Y of hydrophobic character was formed into ⅛" extrudate containing 80% UHP-Y zeolite and 20% peptized $Al_2O_3$ binder. The extrudate was dried at 110° C. and calcined in air at 500° C. 150 grams of the extrudate was soaked in 200 ml of 1.27M (10 vol %) cobalt nitrate, $Co(NO_3)_2$, aqueous acetone solution. The solution was brought to dryness by rotary evaporation. The metal-loaded extrudate was dried at 110° C. and calcined in air at 480° C. for two hours. The anhydrous extrudate contained 8.3 wt % CO. Activation was then carried out in the same manner as in Example II above. In a series of runs, using the resulting cobalt pore-filled catalyst composition, a feed gas mixture of 50 mol % hydrogen and 50 mol % CO was employed with the temperature of the conversion reaction being maintained at about 218°–219° C., with the section pressure being maintained in the range of from about 290 to about 295 psig.

A feed rate of 400 cc of said feed gas/min was employed in each run. The catalyst had an initial weight of 49.6 grams. The conversion results are set forth in Table VII below.

TABLE VII

| Run | 1 | 2 | 3 | 4 | 5 |
|---|---|---|---|---|---|
| Hours on Stream | 6.08 | 24.58 | 30.5 | 55.5 | 75.33 |
| Conversion wt. % | | | | | |
| on CO | 9.96 | 7.13 | 7.48 | 7.11 | 7.45 |
| on $H_2$ | 41.27 | 22.61 | 21.29 | 22.04 | 20.89 |
| on (CO + $H_2$) | 27.25 | 14.81 | 14.37 | 14.92 | 14.22 |
| Product Selectivity, Wt. % | | | | | |
| $CH_4$ | 14.43 | 20.56 | 17.34 | 17.78 | 18.93 |
| $C_2$-$C_4$ | 9.08 | 12.16 | 11.92 | 13.66 | 11.90 |
| $C_5$-420° F. | 60.64 | 48.70 | 48.10 | 45.84 | 55.08 |
| 420° F.-700° F. | 13.07 | 17.08 | 20.60 | 19.38 | 10.92 |
| 700° F.-end point | 2.79 | 1.50 | 2.05 | 3.34 | 3.12 |
| $C_5$-end point | 76.49 | 67.28 | 70.74 | 68.56 | 69.11 |
| Iso/normal mole ratio: | | | | | |
| $C_4$ | 0.5628 | 0.1916 | 0.1818 | 0.1180 | 0.0625 |
| $C_5$ | 1.0050 | 0.3383 | 0.2538 | 0.1772 | 0.1242 |
| $C_6$ | 2.0347 | 0.8870 | 0.7712 | 0.5435 | 0.4462 |

A second set of runs was carried out with the results thereof set forth in Table VIII below. In these runs, catalyst samples utilized as in the runs of Table VII were further used with additional quantities of the same feed gas mixture at the same feed rate, but at a higher temperature level of about 251°–252° C.

TABLE VIII

| Run | 1 | 2 | 3 | 4 | 5 |
|---|---|---|---|---|---|
| Hours on Stream | 78.41 | 95.41 | 102.33 | 119.5 | 126.25 |
| Conversion wt. % | | | | | |
| on CO | 26.16 | 25.34 | 26.02 | 26.05 | 26.81 |
| on $H_2$ | 55.47 | 56.48 | 56.46 | 56.43 | 56.87 |
| on (CO + $H_2$) | 40.83 | 40.98 | 41.45 | 41.43 | 41.96 |
| Product Selectivity, Wt. % | | | | | |
| $CH_4$ | 17.85 | 15.81 | 15.26 | 15.11 | 14.54 |
| $C_2$-$C_4$ | 12.67 | 11.13 | 10.75 | 10.65 | 10.40 |
| $C_5$-420° F. | 51.42 | 47.51 | 53.21 | 46.77 | 51.29 |
| 420° F.-700° F. | 14.05 | 21.25 | 16.17 | 22.67 | 18.39 |
| 700° F.-end point | 4.01 | 4.29 | 4.62 | 4.80 | 5.28 |
| $C_5$-end point | 69.48 | 73.06 | 73.99 | 74.24 | 75.06 |
| Iso/normal mole ratio: | | | | | |
| $C_4$ | 0.1779 | 0.1718 | 0.1617 | 0.1431 | 0.1338 |
| $C_5$ | 0.4215 | 0.3520 | 0.3112 | 0.2866 | 0.2531 |
| $C_6$ | 0.8722 | 0.7599 | 0.5689 | 0.6935 | 0.6801 |

Another set of runs was similarly carried out so as to further extend the hours on stream of the catalyst, with said runs being carried out at 252° C. and at a feed rate of 800 cc/min. The results of such runs are set forth in Table IX below.

TABLE IX

| Run | 1 | 2 | 3 | 4 | 5 |
|---|---|---|---|---|---|
| Hours on Stream | 150.25 | 168.83 | 174.15 | 192.99 | 198.99 |
| Conversion wt. % | | | | | |
| on CO | 20.79 | 18.91 | 20.24 | 19.52 | 19.02 |
| on $H_2$ | 41.13 | 40.61 | 41.29 | 40.90 | 39.55 |
| on (CO + $H_2$) | 31.30 | 30.15 | 31.13 | 30.59 | 29.65 |
| Product Selectivity, Wt. % | | | | | |
| $CH_4$ | 16.07 | 18.07 | 17.04 | 17.78 | 18.02 |
| $C_2$-$C_4$ | 10.60 | 11.21 | 10.75 | 11.20 | 11.29 |
| $C_5$-420° F. | 44.10 | 40.19 | 41.08 | 42.01 | 42.79 |
| 420° F.-700° F. | 21.51 | 22.24 | 22.59 | 21.08 | 20.98 |
| 700° F.-end point | 7.72 | 8.29 | 7.80 | 7.73 | 6.92 |
| $C_4$-end point | 73.33 | 70.72 | 72.71 | 71.02 | 70.69 |
| Iso/normal mole ratio: | | | | | |
| $C_4$ | 0.0913 | 0.0845 | 0.0978 | 0.0788 | 0.0927 |
| $C_5$ | 0.1693 | 0.1384 | 0.1425 | 0.1537 | 0.1391 |
| $C_6$ | 0.5284 | 0.4139 | 0.4184 | 0.4853 | 0.3897 |

In a final series of runs, the hours on stream of the subject cobalt-continuing catalyst of the invention was extended still further, with said runs being carried out at about 252° C. with the exception of run 4 that was carried out at an elevated temperature of 284° C. The results of such runs are summarized in Table X. The feed rate was 480 cc/min for run 3, and 400 cc/min for runs 2–4. It should be noted also that whereas the previous runs described above and summarized in Tables VII, VIII, and IX were carried out using a H:CO ratio of 1:1, the runs set forth in Table X were carried out at a H:CO ratio of 2:1.

TABLE X

| Run | 1 | 2 | 3 | 4 |
|---|---|---|---|---|
| Hours on Stream | 223.25 | 239.75 | 247.50 | 263.92 |
| Conversion wt. % | | | | |
| on CO | 76.82 | 66.83 | 64.50 | 76.35 |
| on $H_2$ | 67.05 | 72.54 | 71.83 | 78.79 |
| on (CO + $H_2$) | 69.89 | 70.60 | 69.37 | 77.95 |
| Product Selectivity, Wt. % | | | | |
| $CH_4$ | 55.31 | 31.81 | 31.11 | 52.82 |
| $C_2$-$C_4$ | 20.07 | 18.68 | 18.55 | 19.36 |
| $C_5$–420° F. | 15.18 | 36.01 | 39.11 | 18.01 |
| 420° F.–700° F. | 6.79 | 8.90 | 8.27 | 4.88 |
| 700° F.–end point | 2.66 | 4.61 | 2.95 | 4.92 |
| $C_5$–end point | 24.61 | 49.51 | 50.34 | 27.82 |
| Iso/normal mole ratio: | | | | |
| $C_4$ | 0.0722 | 0.0566 | 0.0582 | 0.2224 |
| $C_5$ | 0.1175 | 0.1045 | 0.1077 | 0.6701 |
| $C_6$ | 0.2195 | 0.2499 | 0.2736 | 1.4904 |

From the results above, it will be seen that the cobalt-containing catalyst of Example III exhibits somewhat low but steady conversion activity at about 220° C. Higher conversion activity occurs at temperature levels of about 250° C., with the conversion being quite advantageous in view of the low cobalt metal loading of the catalyst. The high $H_2$/CO usage, as reflected by the conversion data, indicates that the catalyst, as with those of previous examples, lacks water gas shift activity. It should be noted that the drop in conversion after 150 hours on stream was actually due to the doubling of the feed rate, and hence of the space velocity, as was indicated with respect to the results set forth in Table IX. After a decrease in conversion after the initial run shown in Table VII, the catalyst actually showed no signs of deactivation over the course of the extended runs described in Tables VII-X. Raising the $H_2$/CO ratio to 2/1 leads to more hydrogen-rich products as will be seen from the results set forth in Table X.

Product selectivity will be seen to be excellent, despite the fact that the methane yield is again quite high. As in the other examples, the methane yield is out of line with the yields of other hydrocarbons, implying that a separate methanation mechanism is operative. It will be appreciated, however, that the $C_5$+ yield is excellent, accounting for over 75% of the hydrocarbon product obtained. Nearly 70% of the hydrocarbons will be observed to boil in the desired motor fuel range, i.e., $C_5$-700° F. A hypothetical catalyst having an exact Schultz-Flory product distribution could produce almost 72% of the product in the motor fuel range. Such a hypothetical catalyst would produce less than 3% methane and almost 9% of hydrocarbon material boiling above 700° F. This catalyst, as similarly the cobalt-containing catalyst of Example II, is thus capable of exceeding the performance of the best possible Schultz-Flory hypothetical product distribution, except for the excess methane production resulting from the practice of the invention using the embodiments of Examples II and III. In this Example III, the most favorable product distribution will be seen to occur at 250° C. with the lower feed rate employed, as was shown in Table VIII. In the practice of the invention, a distinct cut off above $C_{20}$ is found to occur, as evidenced by the lower amounts of material products boiling above 700° F. When the feed rate is doubled at 250° C. under the conditions employed in the example, the yield of gasoline and diesel oil is lowered to about 65%. It will be appreciated that such performance represents an advantageous conversion of syngas to desired liquid motor fuels with relatively minor production of heavy products boiling beyond the diesel oil range.

The quality of the motor fuels produced in the $C_{10}$–$C_{18}$ range, in terms of branched and/or aromatic hydrocarbons suitable for jet and diesel fuels is good while the quality of the gasoline produced does not reach the standards achieved by other known techniques for gasoline production. Isomerization activity of the catalyst begins to demonstrate signs of deactivation at about 250° C., and the catalyst begins to produce some waxy condensed product prior to the increase in space velocity noted with respect to the runs of Table IX.

Those skilled in the art will appreciate that various changes and modifications can be made in the details of the invention as herein described and illustrated without departing from the scope of the invention as set forth in the appended claims. Thus, the conversion of syngas to $C_5$+ hydrocarbon mixtures containing more than 10%, typically more than 20%, of $C_5$+ hydrocarbon molecules comprising $C_{10}$ up to about $C_{22}$ material is advantageously accomplished in a variety of embodiments wherein the catalyst composition comprises a Fischer-Tropsch catalyst together with a co-catalyst/support component as herein described. The product obtained using the novel catalyst composition of the invention frequently contains enhanced amounts of branched and/or aromatic hydrocarbons in addition to n-paraffins and n-olefins. While applicable amounts of methane have been produced in the practice of various embodiments of the invention, it is of significance that only relatively minor amounts of heavy products boiling beyond the diesel oil range are produced. The syngas is thus advantageously converted to hydrocarbons boiling in the gasoline and particularly in the jet fuel and diesel oil range. Such conversion reaction can be carried out at any suitable operating conditions, with the reaction temperature being generally from about 100° C. to about 450° C., generally from about 100° C. to about 400° C. using cobalt-containing catalyst, and from about 150° C. to about 450° C. when iron-containing catalyst is employed, and preferably from about 240° C. to about 320° C. The catalytic conversion reaction is carried out at any desired pressure level, for example at pressures of from about 0 to about 1,000 psig. typically at from about 0 to about 350 psig.

The catalyst composition of the invention can be prepared in any suitable manner known in the art. Thus, Fischer-Tropsch metal can be precipitated or pore filled on the co-catalyst/support component, as in the illustrative examples above, or a physical mixture of said components can be prepared. The amount of said Fischer-Tropsch metal component employed in any particular application of the invention will depend upon the desired operating conditions and particular product specifications pertaining to that application. In general, however, the metal component will be employed in an amount with the range of from about 5% to about 70% by weight based on the overall weight of the catalyst composition, with metal component concentrations of from about 10% to about 50% being generally preferred in most applications. The activating of the Fischer-Tropsch metal component prior to use of the catalyst is carried out by conventional techniques known in the art, such as the techniques referred to with respect to Example I above. Further information regarding the preparation and activation of Fischer-Tropsch catalysts is provided in the published art, as in CATAL.REV.-SCI.ENG., 21(2). 225–274 (1980). "The Fischer-Tropsch Synthesis in the Liquid Phase", by Herbert Kolbel and Miles Ralek, particularly pp. 242–247 thereof.

It will also be appreciated by those skilled in the art that the catalyst composition of the invention may also have a suitable promoter component incorporated therein. Potassium, sodium and thorium are examples of known promoters, with potassium being a generally preferred promoter for purposes of the syngas conversion operations of the invention. Potassium promotion can readily be accomplished by impregnating the metal-loaded steam-stabilized zeolite Y of the invention with a potassium carbonate solution prior to drying and calcining. For example, a catalyst composition of the invention having iron precipitated on UHP-Y zeolite can be prepared by first precipitating the iron on the zeolite by the addition of aqueous ammonia to a boiling slurry of ferric nitrate and said UHP-Y zeolite. After washing and drying the iron-loaded molecular sieve, said molecular sieve can be impregnated with a potassium carbonate solution, dried, pressed into pellets if desired, and air-calcined at 250° C. In another representative example, a physical mixture of iron and zeolite, promoted with potassium, is conveniently prepared from a refluxing solution of 0.05 g/ml of ferric nitrate solution. Iron powder comprising $Fe_2O_3 \times H_2O$ is first precipitated by the addition of a stoichiometric amount of 6N aqueous ammonia. The resulting powder is collected, washed with hot distilled water, e.g. at about 95° C., and dried at 110° C. overnight. The iron powder is then impregnated with $K_2CO_3$ solution and dried. The potassium-promoted catalysts of the examples will contain about 0.7 wt.% $K_2O$ although it will be appreciated that the concentration of potassium or other promoter employed will vary depending upon the Fischer-Tropsch metal and the promoter employed in any particular embodiment. In the latter example above, the potassium-promoted, precipitated iron powder can be ground slightly, mixed with an equal weight of UHP-Y zeolite, pressed into pellets, and air calcined at 250° C. for two hours to produce a metal and co-catalyst support composition comprising a physical mixture of said iron and UHP-Y zeolite containing about 53% iron by weight. The effects of potassium or other promotion are believed to include the introduction of water gas shift activity to the catalyst composition so as to reduce the $H_2/CO$ usage ratio and achieve greater overall syngas conversion. This effect of such promotion appears to be greater with respect to physical mixtures of the catalyst composition than is the case when the Fischer-Tropsch metal component is precipitated on the co-catalyst/support component of the catalyst composition. The potassium-promoted catalysts will in general have a potassium concentration of from about 0.1 to about 5 wt percent of $K_2O$, with sodium-promoted catalysts having a similar concentration range and thorium-promoted catalysts having such a concentration extended up to about 15%.

In the pore-filled catalyst compositions referred to above, the Fischer-Tropsch metal component resides mainly in the large pores between the adsorbent particles. It has also been found possible to place the metal component within the very small pores of the zeolite particles themselves. For this purpose, the zeolite is acid washed or extracted essentially by the process as described in the Eberly patent, U.S. Pat. No. 3,591,488, to remove a large portion of the alumina from its pores prior to treatment to incorporate the metal component therein. By employing a suitable metal-containing liquid, such as an iron cobalt or other suitable metal carbonyl or nitrate, the metal can be positioned within the pores, typically on the order of 10 Angstroms in size, and adsorbed therein to form a co-catalyst/support composition highly advantageous for purposes of the invention. In an illustrative example, UHP-Y molecular sieve zeolite was refluxed in a 13% slurry of said sieve in 3.75M hydrochloric acid for three hours. The slurry was then cooled, and the supernatent was decanted therefrom. The remaining slurry was diluted in half, filtered and washed chloride-free with 0.001M nitric acid. The slurry was then washed with distilled water, dried at 110° C. for 16 hours and then at 250° C. for 16 hours and at 500° C. for an additional two hours and bottled at 400° C. The thus treated material comprises acid-extracted, substantially alumina-free UHP-Y zeolite.

For purposes of the invention, the acid-extracted UHP-Y zeolite was loaded with liquid iron carbonyl, i.e. $Fe(CO)_5$, by impregnation under nitrogen to form a material containing approximately 28% $Fe(CO)_5$. This $Fe(CO)_5$-loaded UHP-Y zeolite was heated to 120° C. in a stream of 0.5% oxygen in nitrogen for three hours, and then at 200° C. for an additional hour. The resulting catalyst composition having the iron positioned within the pores of the zeolite was formed as ⅜" extrudate using 15% silica and 3% KOH as a gelling agent and avicel as an extrusion aid. The extrudates thus formed were dried at 110° C. and combined at 250° C. A plug flow reactor was filled with 50 ml of said co-catalyst/support composition and employed in test runs using CO and hydrogen as a feed gas mixture at various H:CO ratios and processing conditions, with the reactor being employed at 11 bar pressure with the space velocity, or GHSV, being approximately 85 hr$^{-1}$. The results of such runs are shown in Table XI below.

TABLE XI

| Run | 1 | 2 | 3 | 4 | 5 | 6 |
|---|---|---|---|---|---|---|
| Days on Stream | 27 | 44 | 47 | 57 | 69 | 85 |
| Temperature, °C. | 310 | 310 | 310 | 310 | 340 | 340 |
| $H_2$:CO | 1.6 | 0.8 | 0.8 | 1.6 | 1.6 | 1.6 |
| Conversion, wt % | 52.5 | 57.6 | 62.1 | 51.3 | 55.7 | 56.1 |
| Product Selectivity, Wt. % | | | | | | |
| $CH_1$ | 10.8 | 12.2 | 12.1 | 20.7 | 34.7 | 28.9 |
| $C_2$–$C_4$ | 43.9 | 32.9 | 34.0 | 35.3 | 42.3 | 37.5 |
| $C_5$ | 45.3 | 54.9 | 53.9 | 44.0 | 23.0 | 33.6 |

It will be appreciated by those skilled in the art that the catalyst composition thus formed by loading the acid-extracted zeolite from a liquid metal-containing material, and believed to have said metal component positioned within the pores of the zeolite itself, has remarkable stability extending over the long period of time, i.e. nearly three months, covered by said test runs. This will be particularly noted by a comparison of runs 1 and 4, of runs 2 and 3, and of runs 5 and 6 carried out under the same temperature and $H_2$:CO ratio conditions. In each instance, the indicated form of co-catalyst/support composition will be seen to produce an appreciable quantity of $C_5^+$ hydrocarbon molecules.

From the very outstanding stability characteristics referred to above, it will be appreciated that the metal loaded, acid extracted zeolite Y compositions herein disclosed and claimed represent highly advantageous and desirable embodiments of the invention. In the acid extraction of the zeolite, those skilled in the art will appreciate that this pretreatment step is carried out using the process known in the art in a manner that is not destructive of the zeolite structure as characterized by X-ray diffraction and by adsorption measurements. In addition to the hydrochloric acid extraction of the zeolite as illustrated by the example above, it is within the scope of the invention to similarly wash the zeolite with nitric acid or other suitable mineral acids, or with other complexing agents, such as EDTA, i.e. ethylene diamine tetraacetic acid, and the like. As indicated above, the alumina content of the zeolite is typically reduced to less than about 3 weight % or even to about 1 weight % or less based on the overall weight of said thus-treated zeolite, in said aluminum extraction step.

It will also be appreciated that the addition of the Fischer-Tropsch metal component to the acid-extracted zeolite can be accomplished by any known metal loading technique capable of enabling a significant amount of said metal component to be deposited in the co-catalyst/support component, advantageously in the pores of the acid-extracted zeolite itself. In addition to the carbonyl adsorption technique referred to above and illustrated in the example, using cobalt or iron or other suitable carbonyls, it should be noted that other known techniques are suitable for loading the metal component on the acid-extracted UHP-Y zeolite. Such techniques include metal salt impregnation, as with ferric, cobalt or other suitable nitrates, chlorides, cyanides or the like; metal organic impregnation, as with methylcyclopentadienyldicarbonyl and the like; and other known metal loading means, such as by ion exchange means. The highly desirable embodiments of the invention in which the co-catalyst/support component comprises said zeolite Y in acid-extracted form, with the catalyst component loaded thereon, and advantageously positioned within the pores of said acid-extracted zeolite, can thus be prepared by use of a variety of known acid wash and metal loading techniques. The resulting catalyst compositions exhibit remarkably enhanced stability when employed for the desired synthesis gas conversion purpose wherein only relatively minor amounts of heavy products boiling beyond the diesel oil range are produced.

As indicated in the background discussion above, the representative zeolite Y possessing outstanding catalytic properties in petroleum refining applications, i.e. said LZ-Y82, is capable of being used in a Fischer-Tropsch composition for syngas conversion to liquid motor fuels, but without a requisite degree of stability for suitable commercial application. A typical cobalt/LZ-Y82 catalyst composition has been found to have a higher initial activity for syngas conversion than that of the corresponding cobalt/UHP-Y catalyst composition of the invention. After no more than about 167 hours on stream, however, the syngas (CO+$H_2$) conversion activity of the cobalt/LZ-Y82 catalyst is found to be less than that of said cobalt/UHP-Y catalyst. Moreover, while the cobalt/LZ-Y82 catalyst undergoes a sustained deactivation, with the rate of deactivation appearing to increase over the course of continuous processing operations, the rate of deactivation of the cobalt/UHP-Y catalyst of the invention, after the expected, rapid initial deactivation, decreases such that the activity level of said catalyst stabilizes to the point that the catalyst may not be deactivating upon continued further use. Thus, the deactivation characteristics of the cobalt/LZ-Y82 catalyst are very different than those of the cobalt/UHP-Y catalyst of the invention. Such a difference in deactivation characteristics is surprising and unexpected in light of the similarity in crystal structure and chemical composition of the typical zeolite Y, i.e. LZ-Y82, and the particular zeolite Y embodiment, i.e. UHP-Y used in the catalyst composition of the invention. Because of its higher activity after only 7 days on stream and its surprising and unexpectedly lower deactivation rate as compared to the cobalt/LZ-Y82 catalyst, as established by comparative tests, the Fischer-Tropsch/UHP-Y catalyst composition of the invention can be considered for commercial use in fulfillment of the objects expressed above for the invention. As the catalyst composition for practical commercial application should have an operating life at an acceptable activity level of at least two weeks, desirably much longer, the cobalt/LZ-Y82 catalyst composition does not possess a requisite degree of stability to justify its use in the subject syngas conversion operations. Not only does the Fischer-Tropsch catalyst composition of the invention have greater catalytic activity than said cobalt/LZ-Y82 catalyst after only about one-half of the minimum acceptable time for practical commercial operations, on the other hand, but said composition of the invention has a very much lower deactivation rate, perhaps reaching a level of stability in which there is essentially no deactivation at all over the course of continued use extending much longer than said minimum period of acceptable time of operation.

The invention as herein described and claimed provides a highly desirable advance in the art of employing Fischer-Tropsch metals in the conversion of syngas to hydrocarbon products. By employing such Fischer-Tropsch metals in combination with a steam-stabilized, zeolite Y catalyst of hydrophobic character as described and claimed herein, particularly said acid-extracted zeolite, it has been found possible to advantageously convert syngas to hydrocarbons boiling in the gasoline plus jet fuel and diesel oil boiling range. The syngas conversion process of the invention can be carried out using the novel catalyst composition disclosed and claimed so as to produce such desired liquid motor fuels while producing only relatively minor amounts of heavy products boiling beyond the diesel oil range. In some instances, the invention enables the product hydrocarbon molecules comprising $C_{10}$ up to $C_{22}$ material to contain enhanced amounts of the branched and/or aromatic hydrocarbons needed for such fuels. The invention thus enables syngas to be converted to desirable liquid motor fuels in a convenient and practical manner, fulfilling a significant need in the syngas conversion art and providing a highly advantageous approach to the meeting of the increasing motor fuel requirements of industrialized countries throughout the world.

We claim:

1. A catalyst composition adapted for enhanced conversion of synthesis gas comprising carbon monoxide and hydrogen to $C_5^+$ hydrocarbon mixtures having enhanced suitability for use as liquid motor fuels comprising:
   (a) a Fischer-Tropsch catalyst component; and
   (b) a co-catalyst/support component comprising a steam-stabilized, hydrophobic zeolite Y catalyst, whereby said catalyst composition exhibits enhanced stability in the desired synthesis gas conversion, with relatively minor production of heavy products boiling beyond the diesel oil range.

2. The composition of claim 1 in which said zeolite Y catalyst has an $SiO_2/Al_2O_3$ molar ratio equal to or greater than 4.5, the essential X-ray powder diffraction pattern of zeolite Y, a unit cell dimension, $a_o$, of less than 24.45 Angstroms, and a sorptive capacity for water vapor at 25° C. and a $p/p_o$ value of 0.10 of less than 10.0 weight percent.

3. The composition of claim 2 in which said Fischer-Tropsch catalyst comprises iron.

4. The composition of claim 2 in which said Fischer-Tropsch catalyst comprises cobalt.

5. The composition of claim 2 in which said unit cell dimension is from 24.20 to 24.45 Angstroms.

6. The composition of claim 5 in which said $SiO_2/Al_2O_3$ motor ratio of the catalyst is from 4.5 to 20.0.

7. The composition of claim 5 in which the water adsorption capacity of the catalyst, at 25° C. and a $p/p_o$ of 0.10, is less than 4.0 weight percent.

8. The composition of claim 1 in which said co-catalyst/support component comprises said zeolite Y in aluminum-extracted form, said catalyst component being positioned within the pores of said acid-extracted zeolite.

9. The composition of claim 2 in which said zeolite Y is in aluminum-extracted form, said catalyst component being positioned within the pores of said zeolite.

10. The composition of claim 9 in which said Fischer-Tropsch catalyst comprises iron.

11. The composition of claim 9 in which said Fischer-Tropsch catalyst comprises cobalt.

12. The composition of claim 9 in which said aluminum-extracted zeolite has an alumina content of less than about 3 weight %.

13. The composition of claim 12 in which said alumina content is less than about 1 weight %.

14. The composition of claim 12 in which said Fischer-Tropsch catalyst comprises iron.

15. The composition of claim 12 in which said Fischer-Tropsch catalyst comprises cobalt.

16. The composition of claim 1 in which said co-catalyst/support component comprises said zeolite Y in aluminum-extracted form, said catalyst component having been loaded thereon from a liquid Fischer-Tropsch metal-containing material.

17. The composition of claim 16 in which said catalyst component is loaded in the aluminum-extracted zeolite by carbonyl adsorption.

18. The composition of claim 17 in which the alumina content of said aluminum-extracted zeolite is less than about 3 weight %.

19. The composition of claim 18 in which said catalyst component comprises iron.

20. The composition of claim 18 in which said catalyst component comprises cobalt.

21. The composition of claim 18 in which the alumina content of said aluminum-extracted zeolite is less than about 1 weight %.

22. The composition of claim 1 in which said co-catalyst/support component comprises said zeolite Y in aluminum-extracted form, said catalyst component having been loaded thereon by metal salt impregnation.

23. The composition of claim 22 in which the alumina content of said aluminum-extracted zeolite is less than about 3 weight %.

24. The composition of claim 23 in which said catalyst component comprises iron.

25. The composition of claim 23 in which said catalyst component comprises cobalt.

26. The composition of claim 23 in which the alumina content of said aluminum-extracted zeolite is less than about 1 weight %.

27. The composition of claim 1 in which said co-catalyst/support component comprises zeolite Y in aluminum-extracted form, said catalyst component having been loaded thereon by metal organic impregnation.

28. The composition of claim 27 in which the alumina content of said aluminum-extracted zeolite is less than about 3 weight %.

29. The composition of claim 28 in which said catalyst component comprises iron.

30. The composition of claim 28 in which said catalyst component comprises cobalt.

31. The composition of claim 28 in which the alumina content of said aluminum-extracted zeolite is less than about 1 weight %.

32. The composition of claim 1 in which said co-catalyst/support composition comprises said zeolite Y in aluminum-extracted form, said catalyst component having been loaded thereon by ion-exchange.

33. The composition of claim 32 in which the alumina content of said aluminum-extracted zeolite is less than about 3 weight %.

* * * * *